(12) United States Patent
Kuo et al.

(10) Patent No.: US 7,378,532 B2
(45) Date of Patent: May 27, 2008

(54) FUSED PYRAZOLYL COMPOUND

(75) Inventors: Sheng-Chu Kuo, Taichung (TW); Fang-Yu Lee, Tachia Taichung (TW); Che-Ming Teng, Taipei (TW); Li-Jiau Huang, Taichung (TW); Li-Chen Chou, Taichung (TW); Jih-Hwa Guh, Taipei (TW); Shiow-Lin Pan, Taipei (TW)

(73) Assignee: Yung Shin Pharmaceutical Ind. Co., Ltd., Taipei (TW)

( * ) Notice: Subject to any disclaimer, the term of this patent is extended or adjusted under 35 U.S.C. 154(b) by 523 days.

(21) Appl. No.: 10/999,139

(22) Filed: Nov. 29, 2004

(65) Prior Publication Data

US 2005/0215612 A1    Sep. 29, 2005

Related U.S. Application Data

(60) Provisional application No. 60/557,098, filed on Mar. 26, 2004.

(51) Int. Cl.
*C07D 231/56* (2006.01)
*A01N 43/56* (2006.01)

(52) U.S. Cl. .................... 548/361.1; 514/403
(58) Field of Classification Search ............. None
See application file for complete search history.

(56) References Cited

U.S. PATENT DOCUMENTS

| | | | |
|---|---|---|---|
| 6,162,819 A | 12/2000 | Schindler et al. | |
| 6,531,491 B1 | 3/2003 | Kania et al. | |
| 7,226,941 B2 * | 6/2007 | Park et al. .................. | 514/403 |
| 2003/0105336 A1 | 6/2003 | Schindler et al. | |

FOREIGN PATENT DOCUMENTS

| WO | WO 20/83648 A1 | 10/2002 |
|---|---|---|
| WO | WO 03/064397 | 8/2003 |
| WO | WO 20033068754 | 8/2003 |

OTHER PUBLICATIONS

Guzel et al., Bioorg. Med Chem., 14, 2006, 7804-7815.*
Lien et al, J. Med Chem, 45, 2002, 4947-4949.*
Zips et al, "New anticancer agents: in vitro and in vivo", in vivo, 2005, 19, 1-7.*
Lenhart et al., "Binding Structures and Potencies of Oxidosqualene Cyclase Inhibitors with the Homologous Squalene—Hopene Cyclase", J. Med. Chem., 46:2083-2092, 2003.

* cited by examiner

*Primary Examiner*—Kamal A Saeed
*Assistant Examiner*—Sun Jae Y Loewe
(74) *Attorney, Agent, or Firm*—Howrey LLP; Viola T. Kung

(57) ABSTRACT

A fused pyrazolyl compound of the following formula:

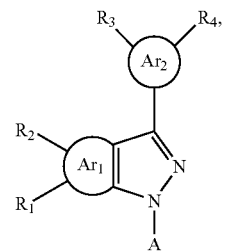

wherein A, $Ar_1$, $Ar_2$, $R_1$, $R_2$, $R_3$, and $R_4$, are as defined herein. Also disclosed is a pharmaceutical composition containing an effective amount of the above-described fused pyrazolyl compound.

24 Claims, No Drawings

FUSED PYRAZOLYL COMPOUND

RELATED APPLICATION

Pursuant to 35 U.S.C. § 119(e), this application claims the benefit of prior U.S. provisional application 60/557,098, filed Mar. 26, 2004.

BACKGROUND

Cancer is an abnormal mass of malignant tissue resulting from uncontrolled excessive cell division. Cancer cells reproduce in defiance of the normal restrains on cell division. They invade and colonize territories normally reserved for other cells. The combination of these actions makes cancer fatal in many instances.

Chemotherapy is one of standard modes in cancer treatment. It is of particular importance for treating inoperable or metastatic forms of cancer. Many chemotherapeutic drugs have been developed. However, there remains a high demand for more effective anti-caner drugs.

SUMMARY

This invention is based on a surprising discovery that a group of novel fused pyrazolyl compounds inhibit cancer cell growth.

An aspect of this invention relates to fused pyrazolyl compounds of Group I. These compounds each have the following formula:

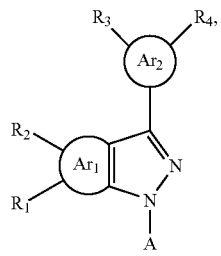

wherein A is

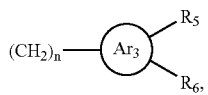

in which n is 0, 1, 2, or 3; each of $Ar_1$, $Ar_2$, and $Ar_3$, independently, is phenyl, thienyl, furyl, pyrrolyl, pyridyl, or pyrimidyl,; and at least one of $R_1$, $R_2$, $R_3$, $R_4$, $R_5$, and $R_6$ is $(CR^aR^b)_pX(CR^cR^d)_qY$, and each of the others, independently, is $R^e$, nitro, halogen, —C(O)OR$^e$, —C(O)SR$^e$, —C(O)NR$^e$R$^f$, —(CH$_2$)$_m$OR$^e$, —(CH$_2$)$_m$SR$^e$, —(CH$_2$)$_m$CN, or —(CH$_2$)$_m$NR$^e$C(O)R$^f$, or $R_1$ and $R_2$ together, or $R_3$ and $R_4$ together, or $R_5$ and $R_6$ together are —O(CH$_2$)$_m$O—; in which X is —O—, —S—, —NR$^{a\prime}$—, —CR$^{a\prime}$R$^{b\prime}$, —O—C (O)—, or —C(O)—O—, each of R$_a$' and R$^{b\prime}$, independently, being H, alkyl, or aryl; Y is —C(O)OR$^{c\prime}$, —NR$^{c\prime}$R$^{d\prime}$, —C(O) NR$^{c\prime}$R$^{d\prime}$SO$_3$R$^{c\prime}$, —SO$_2$NR$^{c\prime}$R$^{d\prime}$, —SONR$^{c\prime}$R$^{d\prime}$, or —P(O) (OR$^{c\prime}$)(OR$^{d\prime}$), each of R$^{c\prime}$ and R$^{d\prime}$ independently, being H, alkyl, or aryl, or NR$^{c\infty}$R$^{d\prime}$ together is a 3-8 membered heterocyclic ring having 1-3 heteroatoms; each of R$^a$, R$^b$, R$^c$, and R$^d$, independently, is H, halogen, nitro, cyano, alkyl, or aryl; R$^e$ and R$^f$ independently, is H, alkyl, or aryl; m is 0, 1, 2, 3, 4, 5, or 6; p is 0, 1, 2, 3, 4, 5, or 6; and q is 1, 2, 3, 4, 5, or 6; or a salt thereof.

A subset of the compounds of Group I feature that $Ar_2$ is 2'-furyl. In some of these compounds, $R_3$ is H and $R_4$ is $(CR^aR^b)_pX(CR^cR^d)_qY$, in which X may be —CR$^{a\prime}$R$^{b\prime}$—, —O—, —S—, —NR$^{a\prime}$—, —O—C(O)—, or —C(O)—O—; and Y may be —NR$^{c\prime}$R$^d$ or —COOH.

Another subset of the compounds of Group I feature that $Ar_1$ is phenyl. In some of these compounds, A is CH$_2$Ph and one of $R_3$ and $R_4$ is $(CR^aR^b)_pX(CR^cR^d)_qY$, in which X may be —CR$^{a\prime}$R$^{b\prime}$, —O—, —S—, —NR$^{a\prime}$—, —O—C(O)—, or —C(O)—O—; and Y may be —COOH or —NR$^{c\prime}$R$^{d\prime}$.

Shown below are a number of exemplary compounds of Group I:

succinic acid mono-[5-(1-benzyl-1H-indazol-3-yl)-furan-2-ylmethyl]ester succinic acid mono-[5-(1-benzyl-1H-indazol-3-yl)-furan-2-ylmethyl]ester, sodium salt succinic acid mono-[5-(1-benzyl-6-methoxy-1H-indazol-3-yl)-furan-2-ylmethyl]ester succinic acid mono-[5-(1-benzyl-5-methoxy-1H-indazol-3-yl)-furan-2-ylmethyl]ester succinic acid mono-[5-(1-benzyl-6-fluoro-1H-indazol-3-yl)-furan-2-ylmethy]ester succinic acid mono-[5-(1-benzyl-6-methyl-1H-indazol-3-yl)-furan-2-ylmethyl]ester succinic acid mono-[5-(1-benzyl-5-methyl-1H-furo[3,2-C]pyrazol-3-yl)-furan-2-ylmethyl]ester succinic acid mono-[5-(1-benzyl-1H-thieno[3,2-C]pyrazol-3-yl)-furan-2-ylmethyl]ester succinic acid mono-[4-(1-benzyl-1H-indazol-3-yl)benzyl]ester succinic acid mono-[5-(1-(4-chloro-benzyl)-1H-indazol-3-yl)-furan-2-ylmethy]ester succinic acid mono-[5-(6-methoxy-1-phenyl-1H-indazol-3-yl)-furan-2-ylmethyl]ester succinic acid mono-[5-(1-(4-bromo-phenyl)-1H-indazol-3-yl)-furan-2-ylmethyl]ester {2-[5-(1-benzyl-1H-indazol-3yl)-furan-2-ylmethoxy]-ethyl}-dimethylamine

[5-(1-benzyl-1H-indazol-3-yl)-furan-2-ylmethoxy]acetic acid

5-[1-benzyl-(5-methylfuro[3,2-C]pyrazol-3-yl)-furan-2-ylmethoxy]acetic acid

3-[5'-(β-dimethylaminoethoxy)methyl-2'-furyl]-5,6-methylenedioxy-1-benzylindazole succinic acid mono-[5-(1-benzyl-1H-indazol-3-yl)-furan-2-ylmethyl]ester, ammonium salt Another aspect of this invention relates to fused pyrazolyl compounds of Group II. These compounds each have the following formula:

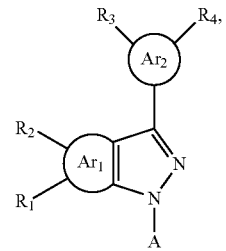

wherein A is H or alkyl; each of Ar₁ and Ar₂, independently, is phenyl, thienyl, furyl, pyrrolyl, pyridyl, or pyrimidyl; and at least one of R₁, R₂, R₃, and R₄ is $(CR^aR^b)_pX(CR^cR^d)_qY$, and each of the others, independently, is $R^e$, nitro, halogen, —C(O)OR$^e$, —C(O)SR$^e$, —C(O)NR$^e$R$^f$, $(CH_2)_mOR^e$, —$(CH_2)_mSR^e$, —$(CH_2)_mCN$, or —$(CH_2)_nNR^eC(O)R^f$, or R₁ and R₂ together, or R₃ and R₄ together, or R₅ and R₆ together are —O(CH₂)$_m$O—; in which X is —O—, —S—, —NR$^{a_1}$—, —CR$^{a_1}$R$^{b_1}$, —O—C(O)—, or —C(O)—O—; each of R$^{a_1}$ and R$^{b_1}$, independently, being H, alkyl, or aryl; Y is —C(O)OR$^{c_1}$, —NR$^{c_1}$R$^{d_1}$, C(O)NR$^{c_1}$R$^{d_1}$, —SO₃R$^{c_1}$, —SO₂NR$^{c_1}$R$^{d_1}$, —SONR$^{c_1}$R$^{d_1}$, or —P(O)(OR$^{c_1}$)(OR$^{d_1}$), each of R$^{c_1}$ and R$^{d_1}$, independently, being H, alkyl, or aryl, or NR$^{c_1}$R$^{d_1}$ together is a 3-8 membered heterocyclic ring having 1-3 heteroatoms; each of R$^a$, R$^b$, R$^c$, and R$^d$, independently, is H, halogen, nitro, cyano, alkyl, or aryl; R$^e$ and R$^f$ independently, is H, alkyl, or aryl; m is 0, 1, 2, 3, 4, 5, or 6; p is 1, 2, 3, 4, 5, or 6; and q is 1, 2, 3, 4, 5, or 6; or a salt thereof.

A subset of the compounds of Group II feature that Ar₂ is 2'-furyl and one of R₃ and R₄ is $(CR^aR^b)_pX(CR^cR^d)_qY$. In some of these compounds, R₃ is H and R₄ is $(CR^aR^b)_pX(CR^cR^d)_qY$ bonded to position 5 of furyl, in which X may be —CR$^{a_1}$R$^{b_1}$, —O—, —S—, —NR$^{a_1}$—, —O—C(O)—, or —C(O)—O—; and Y may be —COOH or —NR$^{c_1}$R$^{d_1}$. Another subset of the compounds of Group II feature that Ar₁ is phenyl.

Another aspect of this invention relates to fused pyrazolyl compounds of Group III. These compounds each have the following formula:

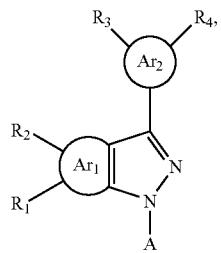

wherein A is

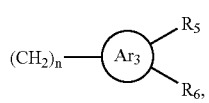

in which n is 0, 1, 2, or 3; each of Ar₁, Ar₂, and Ar₃, independently, is phenyl, thienyl, furyl, pyrrolyl, pyridyl, or pyrimidyl; and at least one of R₁, R₂, R₃, R₄, R₅, and R₆ is $(CR^aR^b)_pX(CR^cR^d)_qY$, and each of the others, independently, is R$^e$, nitro, halogen, —C(O)OR$^e$, —C(O)SR$^e$, —C(O)NR$^e$R, —$(CH_2)_mOR^e$, $(CH_2)_mSR^e$, —$(CH_2)_mCN$, or —$(CH_2)_mNR^eC(O)R^f$, or R₁ and R₂ together, or R₃ and R₄ together, or R₅ and R₆ together are —O(CH₂)$_m$O—; in which X is —C(O)—N—; Y is —C(O)OR$^{c_1}$, R$^{c_1}$ being H, alkyl, or aryl, each of R$^a$, R$^b$, R$^c$, and R$^d$, independently, is H, halogen, nitro, cyano, alkyl, or aryl; R$^e$ and R$^f$ independently, is H, alkyl, or aryl; m is 0, 1, 2, 3, 4, 5, or 6; p is 0, 1, 2, 3, 4, 5, or 6; and q is 1, 2, 3, 4, 5, or 6; or a salt thereof.

A subset of the compounds of Group III feature that Ar₂ is 2'-furyl. In some of these compounds, R₃ is H and R₄ is $(CR^aR^b)_pX(CR^cR^d)_qY$, in which p may be 0, and q may be 1 or 2.

The term "alkyl" refers to a straight or branched hydrocarbon, containing 1-10 carbon atoms. Examples of alkyl groups include, but are not limited to, methyl, ethyl, n-propyl, i-propyl, n-butyl, i-butyl, and t-butyl.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl.

Alkyl and aryl mentioned herein include both substituted and unsubstituted moieties. Examples of substituents include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, and heterocyclyl, in which the alkyl, alkenyl, alkynyl, alkyloxy, aryl, heteroaryl, cyclyl, and heterocyclyl may be further substituted.

The fused pyrazolyl compounds described above include the compounds themselves, as well as their salts. Such a salt, for example, can be formed between a negatively charged substituent (e.g., carboxylate) on a fused pyrazolyl compound and a cation. Suitable cations include, but are not limited to, sodium ion, potassium ion, magnesium ion, calcium ion, zinc ion, and an ammonium cation such as teteramethylammonium ion. Likewise, a positively charged substituent (e.g., ammonium) can form a salt with a negatively charged counterion. Suitable counterions include, but are not limited to, chloride, bromide, iodide, sulfate, nitrate, phosphate, and acetate.

The fused pyrazolyl compounds of this invention can inhibit cancer cell growth. Accordingly, another aspect of the present invention relates to a method of treating cancer, i.e., administering to a subject in need thereof an effective amount of one or more of the fused pyrazolyl compounds. Also within the scope of this invention is a pharmaceutical composition containing an effective amount of one or more of the fused pyrazolyl compounds and a pharmaceutically active carrier, as well as the use of such a composition for the manufacture of a medicament for treating cancer.

Details of several embodiments of the invention are set forth in the description below. Other features, objects, and advantages of the invention will be apparent from the description, and also from the claims.

DETAILED DESCRIPTION

The fused pyrazolyl compounds described above can be synthesized by methods well known in the art. More specifically, a fused pyrazolyl compound having one or more functional groups can be prepared according to methods described in the literature (see, e.g., U.S. Pat. Nos. 5,574,168 and 6,162,819). The fused pyrazolyl compound is further transformed to a compound of this invention by modifying one or more of its functional groups via simple transformations, such as substitution reactions and coupling reactions. Compounds 1, 2, 13, 14, and 17 are synthesized as follows (see also scheme 1):

Phenyl furyl ketone (III) is first prepared by coupling benzoyl chloride (I) with 2-methoxycarbonylfurane (II). The ketone is then reacted with benzylhydrazine (IV) to form hydrazone (V), which is subsequently transformed into an indazolyl compound (VI). The indazolyl compound (VI) has a methoxycarbonyl substitituent at 5'-C of its furyl group.

Reduction of this methoxycarbonyl group affords an alcohol (VII). The alcohol can be transformed to Compound 13 by reacting with β-dimethylaminoethylchloride, and to Compound 14 by reacting with β-chloroacetate followed by hydrolysis. The alcohol (VII) can also be reacted with succinic anhydride to form Compound 1, which may be transformed to a salt, Compound 2 or 17, by reacting with NaOH or NH$_3$.

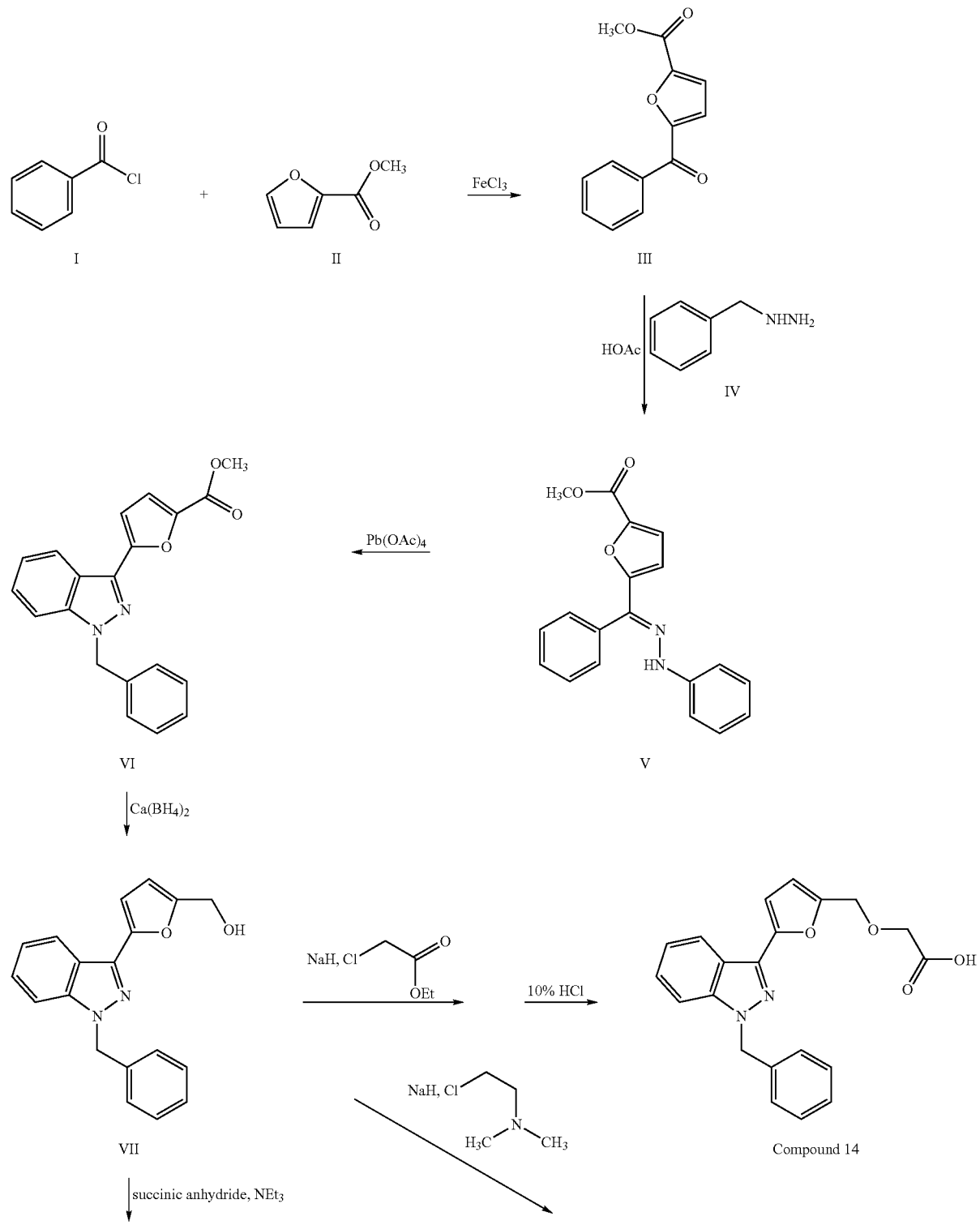

Scheme 1

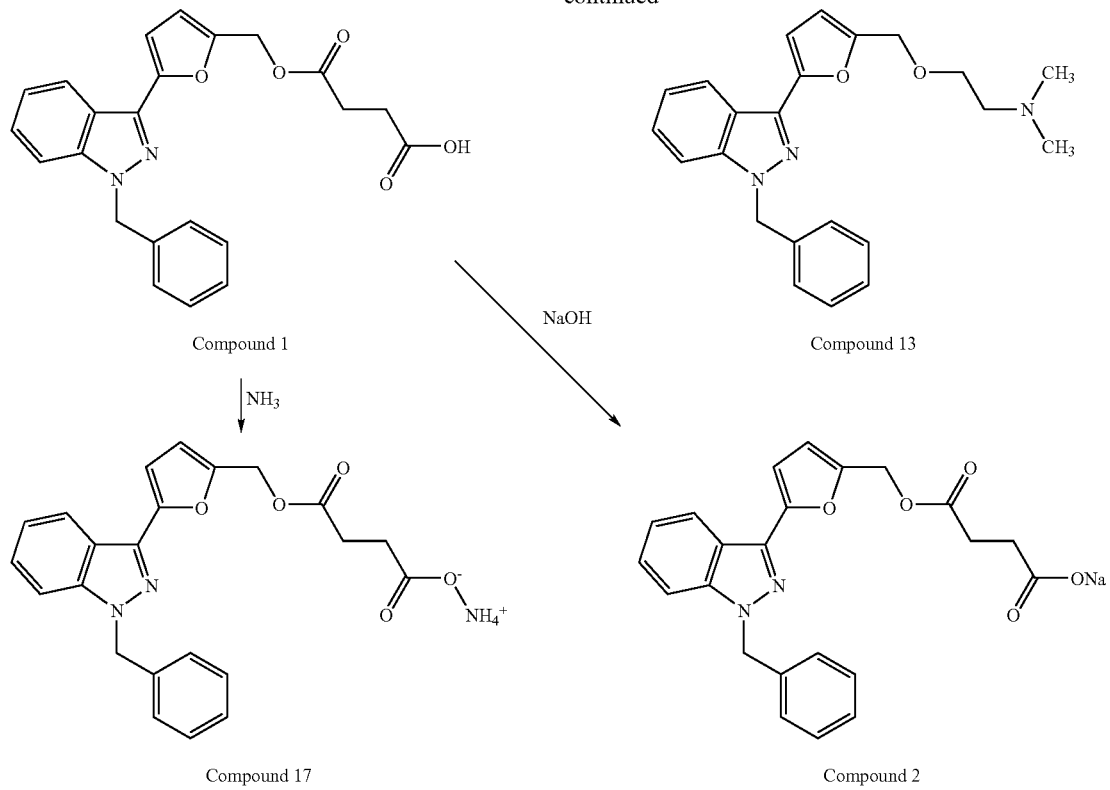

Compound 1

Compound 13

Compound 17

Compound 2

The other compounds of this invention can also be prepared via similar synthetic routes. Details of synthesis of Compounds 1-17 are described in Examples 1-17, respectively.

The chemicals used in the above-described synthetic routes may include, for example, solvents, reagents, catalysts, and protecting group and deprotecting group reagents. The synthetic routes may additionally include steps, either before or after the steps described specifically herein, to add or remove suitable protecting groups in order to ultimately allow synthesis of the desired compounds. In addition, various synthetic steps may be performed in an alternate sequence. Synthetic chemistry transformations and protecting group methodologies (protection and deprotection) useful in synthesizing applicable fused pyrazolyl compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The fused pyrazolyl compounds of this invention are biologically active, i.e., inhibiting cancer cells. Thus, this invention features a pharmaceutical composition that contains an effective amount of a fused pyrazolyl compound of Group I or Group and a pharmaceutically acceptable carrier. "An effective amount" is defined as the amount of a fused pyrazolyl compound which, upon administration to a subject in need thereof, is required to confer the above-described inhibitory effect on the subject. Effective amounts may vary, as recognized by those skilled in the art, depending on route of administration, excipient usage, and the possibility of co-usage with other agents.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound. Examples of other carriers include colloidal silicon oxide, magnesium stearate, cellulose, sodium lauryl sulfate, and D&C Yellow # 10.

The pharmaceutical composition of this invention can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active fused pyrazolyl compounds can also be administered in the form of suppositories for rectal administration.

The fused pyrazolyl compounds of this invention can be preliminarily screened by an in vitro assay for their activity of inhibiting growth of cancer cells. Compounds that demonstrate high activity in the preliminary screening can be further evaluated by in vivo methods well known in the art. For example, a test compound is administered to an animal (e.g., a mouse model) having cancer and its therapeutic effects are then accessed. Based on the results, an appropriate dosage range and administration route can also be determined.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications, including patents, cited herein are hereby incorporated by reference in their entirety.

EXAMPLE 1

Synthesis of succinic acid mono-[5-(1-benzyl-1H-indazol-3-yl)-furan-2-ylmethyl]ester (Compound 1)

(a) Synthesis of 5-methoxycarbonyl-2-furyl phenyl ketone

Anhydrous ferric chloride (0.42 g, 2.6 mmole) and benzoyl chloride (29.6 g, 0.21 mole), were dissolved in $CCl_4$ (40 ml) and added dropwise over 10 min with methyl 2-furoate (25.2 g, 0.20 mmole). The reaction mixture was then heated under reflux for 36 hrs, and after cooling was added with water (120 ml). The mixture was stirred for 1 hr and then allowed to sit until it separated into two layers. The water layer and precipitate were extracted with chloroform. The organic layer was dried over anhydrous magnesium sulfate and then filtered. The solvent of the filtrate was removed under a reduced pressure; the residue was recrystallized from isopropanol to afford 28.4 g 5-methoxycarbonyl-2-furyl phenyl ketone in a yield of 65.0%.

m.p.: 70-73° C.

(b) Synthesis of 1-benzyl-3-(5'-methoxycabonyl-2'-furyl)indazole

5-Methoxycarbonyl-2-furyl phenyl ketone (5.5 g, 0.024 mole) was dissolved in methanol (60 ml), added with benzylhydrazine (9 g, 0.07 mole) and acetic acid (0.5 ml) and then heated under reflux till the reaction was completed. After cooling, the solvent was evaporated. The resultant residue was extracted with chloroform and washed with dilute HCl solution, then water, and then dried over anhydrous magnesium sulfate and filtered. The solvent of the filtrate was removed to give 5-methoxycarbonylfuryl phenyl ketone benzylhydrazone.

A solution of hydrazone thus obtained in dichloromethane (100 ml) was added dropwise to the solution of $Pb(OAc)_4$ (28.2 g, 0.06 mole) in dichloromethane (400 ml). After addition, the mixture was allowed to react at 30±2° C. for 30 min, and $BF_3$·$Et_2O$ (containing 47% of $BF_3$, 122 ml) was added. The mixture was heated under reflux for 30 min and then poured into ice water (1000 ml) to terminate the reaction. The organic layer was separated and washed sequentially with water and 10% sodium carbonate solution, then neutralized by water wash. It was dried over anhydrous magnesium sulfate and was concentrated under vacuum to an oily crude product. Ethanol was then added to the crude product, and the mixture was allowed to precipitate by freeze overnight. The solid precipitate was collected and recrystallized from ethanol to give 3.7 g 1-benzyl-3-(5'-methoxycabonyl-2'-furyl)indazole in a yield of 47%.

m.p.: 117-118° C.

(c) Synthesis of 1-benzyl-3-(5'-hydroxymethyl-2'-furyl)indazole

Calcium borohydride was first prepared by stirring anhydrous calcium chloride (88.8 mg, 0.8 mmole) with sodium borohydride (60 mg, 1.6 mmole) in anhydrous THF (20 mL) for 4 hrs. A 30 mL THF solution containing 88.0 mg 1-benzyl-3-(5'-methoxycarbonyl-2'-furyl)-indazole (0.27 mmole) was then added dropwise to the calcium borohydride solution at 30±2° C. The mixture was heated under reflux for 6 hrs, cooled, quenched into crushed ice, placed at a reduced pressure to remove THF, and filtered to obtain a solid product. The solid was extracted with dichloromethane. The extract was concentrated to 50 mL and a solid precipitated after petroleum ether was added. The precipitate was collected and purified by column chromatography (silica gel-benzene) to obtain 70.0 mg 1-benzyl-3-(5'-hydroxymethyl-2'-furyl)-indazole at a yield of 87%.

m.p.: 108-109° C.;

MS: m/z: 304 ($M^+$);

IR(KBr) $v_{max}$: 3350 $cm^{-1}$ (—OH);

$^1$H-NMR(DMSO-d6, 200 MHz) δ: 4.51 (2H, d, J=5.5 Hz, —$CH_2$O—), 5.31 (1H, t, J=5.5 Hz, —OH), 5.70 (2H, s, —$CH_2C_6H_5$), 6.47 (1H, d, J=3.4 Hz, C4'-H), 6.95 (1H, d, J=3.4 Hz, C3'-H), 7.21-7.31 (6H, m, C5, Ar—H), 7.45 (1H, t, J=8.2 Hz, C6-H), 7.75 (1H, dd, J=8.2, 1.8 Hz, C7-H), 8.12 (1H, dd, J=8.2, 1.0 Hz, C4-H).

(d) Synthesis of Succinic acid mono-[5-(1-benzyl-1H-indazol-3-yl)-furan-2-yl-methyl]ester 1-Benzyl-3-(5'-hydroxymethyl-2'-furyl)indazole (1.824 g, 6 mmole) and triethylamine (1.010 g, 10 mmole) were dissolved in THF (15 ml). A solution of succinic anhydride (660 mg, 6.6 mmole) in THF (30 ml) was added dropwise over 30 min under reflux. After the reaction was completed, the solvent was removed by evaporation. The residue was purified by a silica gel column, eluting with EtOAc/n-hexane. Compound 1 was obtained in a yield of 80%.

MS: m/z: 404(M$^+$);

IR(KBr) $v_{max}$: 3500~2500 cm$^{-1}$ (—COOH); 1740 cm$^{-1}$ (—C=O);

$^1$H-NMR(CDCl$_3$, 200 MHz) δ: 2.67 (4H, s, —COCH$_2$—), 5.22 (2H, s, —OCH$_2$—), (2H, s, —CH$_2$C$_6$H$_5$), 6.56 (1H, d, J=3.3 Hz, C4'-H), 6.87 (1H, d, J=3.3 Hz, C3'-H), 7.19-7.36 (7H, m, Ar, C5, C6, C7-H), 8.04 (1H, d, J=7.9 Hz, C4-H);

Anal. Calc. for C$_{23}$H$_{20}$N$_2$O$_5$: C, (68.31); H, (4.98); N, (6.93);

Found: C (68.35); H, (4.90); N, (6.90).

EXAMPLE 2

Synthesis of succinic acid mono-[5-(1-benzyl-1H-indazol-3-yl)-furan-2-ylmethyl]ester, sodium salt (Compound 2)

Compound 1 (170 mg, 0.4 mmle) was treated with NaOH (16 mg, 0.38 mmole) in 0.5 ml H$_2$O, in 10 ml EA at 0° C. The reaction mixture was extracted with 1:1H$_2$O/EA. The aqueous layer was evaporated to afford Compound 2 in a yield of 78%.

MS: m/z: 426 (M$^+$);

IR(KBr) $v_{max}$:1770 cm$^{-1}$ (C=O);

$^1$H-NMR(DMSO-d6, 200 MHz) δ: 2.16(2H, d, J=6.8 Hz, —CH$_2$CO$_2$Na); 2.40(2H, d, J=6.8 Hz, —COCH$_2$—); 5.12 (2H, s, —OCH$_2$—); 5.71(2H, s, —CH$_2$C$_6$H$_5$); 6.69(1H, d, J=3.3 Hz, C4'-H); 7.00(1H, d, J=3.3 Hz, C3'-H); 7.22-7.45 (7H, m, C5, C6, Ar—H); 7.72(1H, d, J=8.3 Hz, C7-H); 8.07(1H, d, J=8.1 Hz, C4-H);

Anal. Calc. For C$_{23}$H$_{19}$N$_2$NaO$_5$=C (64.79); H, (4.49); N, (6.57);

Found: C, (64.77); H, (4.46); N, (6.52).

EXAMPLE 3

Synthesis of succinic acid mono-[5-(1-benzyl-6-methoxy-1H-indazol-3-yl)-furan-2-ylmethyl]ester (Compound 3)

(a) Synthesis of 1-benzyl-3-(5'-hydroxymethyl-2'-furyl)-6-methoxyindazole

Reactions were carried out according to the same procedures described in Example 1 (a), (b), and (c), except that 4-methoxybenzoyl chloride was used instead of benzoyl chloride. 1-Benzyl-3-(5'-hydroxymethyl-2'-furyl)-6-methoxyindazole was obtained in a yield of 77%.

m.p.: 109-110° C.;

MS: m/z: 334(M$^+$);

IR(KBr) $v_{max}$: 3300~3400 cm$^{-1}$ (—OH);

$^1$H-NMR(CDCl$_3$, 200 MHz) δ: 1.90 (1H, br, —OH), 3.80 (3H, s, —CH$_3$), 4.74 (2H, d, J=4.9 Hz, —CH$_2$—O—), 5.59 (2H, s, —CH$_2$C$_6$H$_5$), 6.47 (1H, d, J=3.2 Hz, C4'-H), 6.59 (1H, d, J=2.0 Hz, C7-H), 6.84 (1H, d, J=3.2 Hz, C3'-H), 6.88 (1H, dd, J=8.5, 1.5 Hz, C5-H), 7.17-7.31 (5H, m, Ar—H), 7.91 (1H, d, J=8.5 Hz, C4-H);

Anal. Calc. For C$_{20}$H$_{18}$N$_2$O$_3$: C, (71.84); H, (5.43); N, (8.38);

Found: C, (71.60); H, (5.48); N, (8.30);

(b) Synthesis of succinic acid mono-[5-(1-benzyl-6-methoxy-1H-indazol-3-yl)-2-ylmethyl]ester 1-Benzyl-3-(5'-hydroxymethyl-2'-furyl)-6-methoxyindazole was reacted with succinic anhydride according the procedure described in Example 1 (d) to afford Compound 3 in yield of 74%.

MS: m/z: 434(M$^+$);

IR(KBr) $v_{max}$: 3500~2550 cm$^{-1}$ (—COOH); 1728 cm$^1$ (—C=O);

$^1$H-NMR(CDCl$_3$, 200 MHz) δ: 2.68(4H, s, —COCH$_2$—); 3.86(3H, s, —CH$_3$); 5.49(2H, s, —OCH$_2$—) 5.61(2H, s, —CH$_2$C$_6$H$_5$); 6.54(1H, d, J=3.2 Hz, C4'-H); 6.62(1H, d, J=2.0 Hz, C7-H); 6.84(1H, d, J=3.2 Hz, C3'-H); 6.89(1H, dd, J=8.5, 1.5 Hz, C5-H); 7.20-7.42(5H, m, Ar—H); 7.93(1H, d, J=8.5 Hz, C4-H);

Anal. Calc. For C$_{24}$H$_{22}$N$_2$O$_6$: C, (66.35); H, (5.10); N, (6.45);

Found: C, (66.40); H, (5.05); N, (6.32).

EXAMPLE 4

Synthesis of succinic acid mono-[5-(1-benzyl-5-methoxy-1H-indazol-3-yl)-furan-2-ylmethyl]ester (Compound 4)

(a) Synthesis of 1-benzyl-3-(5'-hydroxymethyl-2'-furyl)-5-methoxyindazole

Reactions were carried out according to the same procedures described in Example 1 (a), (b), and (c), except that 3-methoxybenzoyl chloride was used instead of benzoyl chloride. 1-Benzyl-3-(5'-hydroxymethyl-2'-furyl)-5-methoxyindazole was obtained in a yield of 77%.

m.p.: 134-135° C.;

MS: m/z: 334 (M$^+$);

IR(KBr) $v_{max}$: 33003400 cm$^{-1}$ (—OH);

$^1$H-NMR(DMSO-d6, 200 MHz) δ: 3.84 (3H, s, —OCH$_3$), 4.50 (2H, d, J=5.8 Hz, —CH$_2$—OH), 5.36 (1H, t, J=5.81 Hz, —OH), 5.65 (2H, s, —CH$_2$C$_6$H$_5$), 6.47 (1H, d, J=3.2 Hz, C4'-H), 6.96 (1H, d, J=3.2 Hz, C3'-H), 7.10 (1H, dd, J=9.1, 2.2 Hz, C6-H), 7.19-7.30 (5H, m, Ar—H), 7.40 (1H, d, J=2.2 Hz, C4-H), 7.65 (1H, d, J=9.1 Hz, C7-H);

Anal. Calc. for C$_{20}$H$_{18}$N$_2$O$_3$: C, (71.84); H, (5.43); N, (8.38);

Found: C, (72.12); H, (5.30); N, (8.52).

(b) Synthesis of succinic acid mono-[5-(1-benzyl-5-methoxy-1H-indazol-3-yl)-furan-2-ylmethyl]ester 1-Benzyl-3-(5'-hydroxymethyl-2'-furyl)-5-methoxyindazole reacted with succinic anhydride according the procedure described in Example 1 (d) to afford Compound 4 in a yield of 68%.

MS: m/z: 434(M$^+$);

IR(KBr) $v_{max}$: 3500~2530 cm$^{-1}$ (—COOH); 1768 cm$^{-1}$ (C=O);

$^1$H-NMR(CDCl$_3$, 200 MHz) δ: 2.69 (4H, s, —COCH$_2$—), 3.90 (3H, s, —OCH$_3$), 525 (2H, s, —OCH$_2$—), 5.62 (2H, s, —CH$_2$C$_6$H$_5$), 6.55 (1H, d, J=3.2 Hz, C4'-H), 6.80 (1H, d, J=3.3 Hz, C3'-H), 7.05-7.30 (8H, m, Ar—H); Anal. Calc. for C$_{24}$H$_{22}$N$_2$O$_6$: C, (66.35); H, (5.10); N, (6.45);

Found: C, (66.05); H, (5.06); N, (6.38).

EXAMPLE 5

Synthesis of succinic acid mono-[5-(1-benzyl-6-fluoro-1H-indazol-3-yl)-furan-2-ylmethy]ester (Compound 5)

(a) Synthesis of 1-benzyl-3-(5'-hydroxymethyl-2'-furyl)-6-fluoroindazole

Reactions were carried out according to the same procedures described in Example 1 (a), (b), and (c), except that 4-fluorobenzoyl chloride was used instead of benzoyl chloride. 1-Benzyl-3-(5'-hydroxymethyl-2'-furyl)-6-fluoroindazole was obtained in a yield of 88% m.p.: 110-112° C.;
MS: m/z: 322 (M$^+$);
IR(KBr) $v_{max}$: 3300~3345 cm$^{-1}$ (—OH);
$^1$H-NMR(DMSO-d6, 200 MHz) δ: 4.49 (2H, br, —CH$_2$—OH), 5.45 (1H, br, —OH), 5.88 (2H, s, —CH$_2$C$_6$H$_5$), 6.48 (1H, d, J=3.2 Hz, C4'-H), 6.98 (1H, d, J=3.2 Hz, C3'-H), 7.10-7.18 (1H, m, C5-H), 7.24-7.36 (5H, m, Ar—H), 7.70 (1H, dd, J=8.5, 5.1 Hz, C4-H);
Anal. Calc. for C$_{19}$H$_{15}$FN$_2$O$_2$: C, (70.80); H, (4.69); N, (8.69);
Found: C, (70.68); H, (4.68); N, (8.55).

(b) Synthesis of succinic acid mono-[5-(1-benzyl-6-fluoro-1H-indazol-3-yl)-furan-2-ylmethy]ester 1-Benzyl-3-(5'-hydroxymethyl-2'-furyl)-6-fluoroindazole was reacted with succinic anhydride according to the procedure described in Example 1(d) to afford Compound 5 in a yield of 72%.

m.p.: 120.5-121.8° C.;
MS: m/z: 422(M$^+$);
IR(KBr) $v_{max}$: 3300~2500 cm$^{-1}$ (COOH); 1737 cm$^{-1}$ (C=O);
$^1$H-NMR(CDCl$_3$, 200 MHz) δ: 2.69 (4H, s, —COCH$_2$—), 5.22 (2H, s, —OCH$_2$—), 5.58 (2H, s, —CH$_2$C$_6$H$_5$), 6.55 (1H, d, J=3.3 Hz, C4'-H), 6.86-7.36 (7H, m, Ar, C3', C5, C7-H), 7.98 (1H, dd, J=6.8, 1.9 Hz, C4-H);
Anal. Calc. for C$_{23}$H$_{19}$FN$_2$O$_5$: C, (65.40); H, (4.53); N, (6.63);
Found: C, (65.32); H, (4.50); N, (6.67).

EXAMPLE 6

Synthesis of succinic acid mono-[5-(1-benzyl-6-methyl-1H-indazol-3-yl)-furan-2-ylmethyl ester (Compound 6)

(a) Synthesis of 1-benzyl-3-(5'-hydroxymethyl-2'-furyl)-6-methylindazole

Reactions were carried out according to the same procedures described in Example 1 (a), (b), and (c), except that 4-methylbenzoyl chloride was used instead of benzoyl chloride. 1-Benzyl-3-(5'-hydroxymethyl-2'-furyl)-6-methylindazole was obtained in a yield of 80%.

m.p.: 112-114° C.;
MS: m/z: 318 (M$^+$);
IR(KBr) $v_{max}$: 3300~3400 cm$^{-1}$ (—OH);
$^1$H-NMR(DMSO-d6, 200 MHz) δ: 2.44 (3H, s, —CH$_3$), 4.50 (2H, d, J=5.2 Hz, —CH$_2$—O—), 5.30 (1H, br, —OH), 5.64 (2H, s, —CH$_2$C$_6$H$_5$), 6.45 (1H, d, J=3.3 Hz, C4'-H), 6.92 (1H, d, J=3.3 Hz, C3'-H), 7.08 (1H, dd, J=8.3, 1.0 Hz, C5-H), 7.19-7.36 (5H, m, Ar—H), 7.52 (1H, d, J=1.0 Hz, C7-H), 7.98 (1H, dd, J=8.3, 1.0 Hz, C4-H);
Anal. Calc. for C$_{20}$H$_{18}$N$_2$O$_2$: C, (75.45); H, (5.70); N, (8.80);
Found: C, (75.20); H, (5.68); N, (8.76).

(b) Synthesis of succinic acid mono-[5-(1-benzyl-6-methyl-1H-indazol-3-yl)-furan-2-ylmethyl ester (Compound 6)

1-Benzyl-3-(5'-hydroxymethyl-2'-furyl)-6-methylindazole was reacted with succinic anhydride according the procedure described in Example 1 (d) to afford Compound 6 in a yield of 80%.

m.p.: 122.6-125.6° C.;
MS: m/z: 418 (M$^+$);
IR(KBr) $v_{max}$: 3500~250 cm$^{-1}$ (COOH); 1718 cm$^{-1}$ (C=O);
$^1$H-NMR(CDCl$_3$, 200 MHz) δ: 2.34 (3H, s —CH$_3$), 2.68 (4H, s, —COCH$_2$—), 5.22 (2H, s, —OCH$_2$—), 5.62 (2H, s, —CH$_2$C$_6$H$_5$), 6.55 (1H, d, J=3.3 Hz, C4'-H), 6.87 (1H, d, J=3.3 Hz, C3'-H), 7.04-7.32 (7H, m, Ar, C5, C7-H), 7.89 (1H, d, J=8.3 Hz, C4-H);
Anal. Calc. for C$_{24}$H$_{22}$N$_2$O$_5$: C, (68.89); H, (5.30); N, (6.69);
Found for C;: C, (68.82); H, (5.31); N, (6.63).

EXAMPLE 7

Synthesis of succinic acid mono-[5-(1-benzyl-5-methyl-1H-furo[3,2-C]pyrazol-3-yl)-furan-2-ylmethyl]ester (Compound 7)

(a) Synthesis of 1-benzyl-3-(5'-hydroxymethyl-2'-furyl)-5-methylfuro[3,2-C]-pyrazole Reactions were carried out according to the same procedures described in Example 1 (a), (b), and (c), except that 5-methyl-furylcarbonyl chloride was used instead of benzoyl chloride. 1-Benzyl-3-(5'-hydroxymethyl-2'-furyl)-5-methylfuro[3,2-C]-pyrazole was obtained in a yield of 75% m.p.: 117-119° C.;
MS: m/z: 308 (M$^+$);
IR(KBr) $v_{max}$: 3300~3400 cm$^{-1}$ (—OH);
$^1$H-NMR(DMSO-d6, 200 MHz) δ: 2.36 (3H, s, —CH$_3$), 4.43 (2H, d, J=5.7 Hz, —CH$_2$O—), 5.33 (1H, t, J=5.7 Hz, —OH), 5.35 (2H, s, —CH$_2$C$_6$H$_5$), 6.25 (1H, s, C6-H), 6.40 (1H, d, J=3.2 Hz, C4'-H), 6.60 (1H, d, J=3.2 Hz, C3'-H), 7.29-7.33 (5H, m, Ar—H);
Anal. Calc. for C$_{18}$H$_{16}$N$_2$O$_3$: C, (70.12); H, (5.23); N, (9.09);
Found: C, (70.16); H, (5.25); N, (9.01).

(b) Synthesis of succinic acid mono-[5-(1-benzyl-5-methyl-1H-furo[3,2-C]pyrazol-3-yl)-furan-2-ylmethyl]-ester (Compound 7)

1-Benzyl-3-(5'-hydroxymethyl-2'-furyl)-5-methylfuro[3,2-C]-pyrazole reacted with succinic anhydride according the procedure described in Example 1 (d) to afford Compound 7 in a yield of 75%.

m.p.: 126.3-129° C.;
MS: m/z: 408 (M$^+$);
IR(KBr) $v_{max}$: 3500~2500 cm$^{-1}$ (—COOH); 1761 cm$^{-1}$ (C=O)
$^1$H-NMR(CDCl$_3$, 200 MHz) δ: 2.34 (3H, s, —CH$_3$), 2.68 (4H, s, —COCH$_2$—), 4.68 (1H, br, OH), 5.19 (2H, s, —CH$_2$—O—), 5.36 (2H, s, —CH$_2$C$_6$H$_5$), 5.59 (1H, s, C6-H), 6.50 (1H, d, J=3.3 Hz, C4'-H), 6.69 (1H, d, J=3.3 Hz, C3'-H), 7.27-7.38 (5H, m, Ar—H);
Anal. Calc. for C$_{22}$H$_{20}$N$_2$O$_6$: C, (64.70); H, (4.94); N, (6.86);
Found: C, (64.92); H, (4.69); N, (6.53).

EXAMPLE 8

Synthesis of succinic acid mono-[5-(1-benzyl-1H-thieno[3,2-C]pyrazol-3-yl)-furan-2-ylmethyl]ester (Compound 8)

(a) Synthesis of 1-benzyl-3-(5'-hydroxymethyl-2'-furyl)thieno[3,2-C]pyrazole

Reactions were carried out according to the same procedures described in Example 1 (a), (b), and (c), except that 4-methoxybenzoyl chloride was used instead of benzoyl chloride. 1-Benzyl-3-(5'-hydroxymethyl-2'-furyl)thieno[3,2-C]pyrazole was obtained in a yield of 76%.

m.p.: 103-104° C.;
MS: m/z: 310 (M$^+$);
IR(KBr) $v_{max}$: 3300~3360 cm$^{-1}$ (—OH);
$^1$H-NMR(DMSO-d6, 200 MHz) δ: 4.46 (2H d, J=5.3 Hz, —CH$_2$—O—), 5.27 (1H, t, J=5.3 Hz, —OH), 5.55 (2H, s, —CH$_2$C$_6$H$_5$), 6.43 (1H, d, J=3.2 Hz, C4'-H), 6.64 (1H, d, J=3.2 Hz, C3'-H), 7.20 (1H, d, J=4.8 Hz, C6-H), 7.27-7.35 (5H, m, Ar—H), 7.72 (1H, d, J=4.8 Hz, C5-H);

Anal. Calc. for C$_{17}$H$_{14}$N$_2$O$_2$S: C, (65.79); H, (4.55); N, (9.03);
Found: C, (65.70); H, (4.53); N, (9.13).

(b) Synthesis of Succinic acid mono-[5-(1-benzyl-1H-thieno[3,2-C]pyrazol-3-yl)-furan-2-ylmethyl]ester (Compound 8)

1-Benzyl-3-(5'-hydroxymethyl-2'-furyl)thieno[3,2-C]pyrazole was reacted with succinic anhydride according the procedure described in Example 1 (d) to afford Compound 8 in a yield of 84%.

MS: m/z: 410 (M$^+$);
IR(KBr) $v_{max}$: 3500~2550 cm$^{-1}$ (—COOH); 1742 cm$^1$ (C=O)
$^1$H-NMR(DMSO-d$_6$, 200 MHz) δ: 2.69(4H, s, —CH$_2$CO—); 5.20(2H, s, —CH$_2$—O—); 5.52(2H, s, —CH$_2$C$_6$H$_5$); 6.50(1H, d, J=3.3 Hz, C4'-H); 6.57(1H, d, J=5.3 Hz, C6-H); 6.63(1H, d, J=3.3 Hz, C3'-H); 7.25-7.37 (6H, m, C5-H, Ar—H);

Anal. Calc. for C$_{21}$H$_{18}$N$_2$O$_5$S: C, (61.45); H, (4.42); N, (6.83);
Found: C, (61.49); H, (4.38); N, (6.80).

EXAMPLE 9

Synthesis of succinic acid mono-[4-(1-benzyl-1H-indazol-3-yl)benzyl]ester (Compound 9)

(a) Synthesis of 1-benzyl-3-(4'-hydroxymethylphenyl)indazole

Reactions were carried out according to the same procedures described in Example 1 (a), (b), and (c), except that hydroxymethylbenzene was used instead of methyl 2-furoate. 1-Benzyl-3-(4'-hydroxymethylphenyl)indazole was obtained in a yield of 81%.

m.p.: 110-112° C.;
MS: m/z: 314 (M$^+$);
IR(KBr) $v_{max}$: 3300~3500 cm$^{-1}$ (—OH);
$^1$H-NMR(DMSO-d6, 200 MHz) δ: 4.58 (2H, d, J=5.2 Hz, —CH$_2$O—), 5.31 (1H, t, J=5.2 Hz, —OH), 5.73 (2H, S, —CH$_2$C$_6$H$_5$), 7.23-8.17 (13H, m, Ar—H);

Anal. Calc. for C$_{21}$H$_{18}$N$_2$O: C, (80.23); H, (5.77); N, (8.91);
Found: C, (80.02); H, (5.75); N, (8.94).

(b) Synthesis of succinic acid mono-[4-(1-benzyl-1H-indazol-3-yl)benzyl]ester (Compound 9)

1-Benzyl-3-(4'-hydroxymethylphenyl)indazole was reacted with succinic anhydride according the procedure described in Example 1 (d) to afford Compound 9 in a yield of 75%.

MS: m/z: 414 (M$^+$);
IR(KBr) $v_{max}$: 3500~2500 cm$^{-1}$ (—COOH); 1750 cm$^1$ (C=O);
$^1$H-NMR(CDCl$_3$, 200 MHz) δ: 2.71 (4H, s, —COCH$_2$—), 5.21 (2H, s, —OCH$_2$C$_6$H$_4$—), 5.66 (2H, s, —CH$_2$C$_6$H$_5$), 7.18-7.51 (11H, m, Ar—H), 7.97-8.04 (3H, m, Ar—H);

Anal. Calc. For C$_{25}$H$_{22}$N$_2$O$_4$: C, (72.45); H, (5.35); N, (6.76);
Found: C, (72.40); H, (5.37); N, (6.70).

EXAMPLE 10

Synthesis of succinic acid mono-[5-(1-(4-chlorobenzyl)-1H-indazol-3-yl)-furan-2-ylmethy]ester (Compound 10)

(a) Synthesis of 1-(p-chlorobenzyl)-3-(5'-hydroxymethyl-2'-furyl)indazole

Reactions were carried out according to the same procedures described in Example 1 (a), (b), and (c), except that p-chlorobenzylhydrozine was used instead of benzylhydrozine. 1-(p-Chlorobenzyl)-3-(5'-hydroxymethyl-2'-furyl)indazole was obtained in a yield of 70%.

MS: m/z: 338 (M$^+$);
IR(KBr) $v_{max}$: 3400~3350 cm$^{-1}$ (—OH);
$^1$H-NMR(CDCl$_3$, 200 MHz) δ: 4.67 (2H, s, —CH$_2$OH), 5.64 (2H, s, —CH$_2$C$_6$H$_5$), 6.39 (1H, d, J=3.4 Hz, C4'-H), 6.58-7.36 (7H, m, Ar—H), 7.84 (1H, d, J=8.9, C4-H);

Anal. Calc. for C$_{19}$H$_{15}$ClN$_2$O$_2$: C, (67.36); H, (4.46); N, (8.27);
Found: C, (67.30); H, (4.45); N, (8.29).

(b) Synthesis of succinic acid mono-[5-(1-(4-chloro-benzyl)-1H-indazol-3-yl)-furan-2-ylmethy]ester (Compound 10)

1-(p-Chlorobenzyl)-3-(5'-hydroxymethyl-2'-furyl)indazole was reacted with succinic anhydride according the procedure described in Example 1 (d) to afford Compound 10 at a yield of 83%.

MS: m/z: 438 (M$^+$);
IR(KBr) $v_{mx}$: 3500~2550 cm$^{-1}$ (—COOH); 1748 cm$^{-1}$ (C=O);
$^1$H-NMR(CDCl$_3$, 200 MHz) δ: 2.68 (4H, s, —COCH$_2$—), 5.23 (2H, s, —OCH$_2$—), 5.61 (2H, s, —CH$_2$C$_6$H$_5$), 6.56 (1H, d, J=3.3 Hz, C4'-H), 6.87 (1H, d, J=3.3 Hz, C3'-H), 7.12-7.39 (7H, m, Ar, C5, C6, C7-H), 8.04 (1H, d, J=7.9 Hz, C4-H);

Anal. Calc. for C$_{23}$H$_{19}$ClN$_2$O$_5$: C, (62.95); H, (4.36); N, (6.38);
Found: C, (62.98); H, (4.33); N, (6.42).

EXAMPLE 11

Succinic acid mono-[5-(6-methoxy-1-phenyl-1H—indazol-3-yl)-1-furan-2-ylmethyl]ester (Compoun 11)

(a) Synthesis of 1-phenyl-3-(5'-hydroxymethyl-2'-furyl)-6-methoxyindazole

Reactions were carried out according to the same procedures described in Example 1 (a), (b), and (c), except that 4-methoxybenzoyl chloride and phenylhydrazine were used instead of benzoyl chloride and benzylhydrazine chloride, respectively. 1-Phenyl-3-(5'-hydroxymethyl-2'-furyl)-6-methoxyindazole was obtained in a yield of 70%

MS: m/z: 320 ($M^+$);

IR(KBr) $v_{max}$: 3450~3300 $cm^{-1}$ (—OH);

$^1$H-NMR(CDCl$_3$, 200 MHz) δ: 3.87 (3H, s, —OCH$_3$), 4.75 (2H, s, —CH$_2$OH), 6.47 (1H, d, J=3.3 Hz, C4'-H), 6.92-7.76 (7H, m, Ar—H), 7.99 (1H, d, J=8.8 Hz, C4-H);

Anal. Calc. for $C_{19}H_{16}N_2O_3$: C, (71.24); H, (5.03); N, (8.74);

Found: C, (71.31); H, (5.06); N, (8.70).

(b) Synthesis of succinic acid mono-[5-(6-methoxy-1-phenyl-1H—-indazol-3-yl)-furan-2-ylmethyl]ester (Compound 11)

1-Phenyl-3-(5'-hydroxymethyl-2'-furyl)-6-methoxyindazole was reacted with succinic anhydride according the procedure described in Example 1 (d) to afford Compound 11 in a yield of 78%.

MS: m/z: 420 ($M^+$);

IR(KBr) $v_{max}$: 3300~2500 $cm^{-1}$ (COOH); 1736 $cm^{-1}$ (C=O);

$^1$H-NMR(CDCl$_3$, 200 MHz) δ: 2.69 (4H, s, —COCH$_2$—), 3.87 (3H, s, —OCH$_3$), 5.23 (2H, s, —OCH$_2$—), 6.56 (1H, d, J=3.4 Hz, C4'-H), 6.92-7.76 (7H, m, Ar, C3', C5, C7-H), 7.96 (1H, d, J=9.0 Hz, C4-H);

Anal. Calc. for $C_{23}H_{20}N_2O_6$: C, (65.71); H, (4.79); N, (6.66);

Found: C, (65.66); H, (4.76); N, (6.61).

EXAMPLE 12

Synthesis of succinic acid mono-[5-(1-(4-bromo-phenyl)-1H-indazol-3-yl)-furan-2-ylmethyl]ester (Compound 12)

(a) Synthesis of 1-(p-bromophenyl)-3-(5'-hydroxymethyl-2'-furyl)indazole

Reactions were carried out according to the same procedures described in Example 1 (a), (b), and (c), except that 4-bromophenylhydrazine was used instead of benzylhydrazine. 1-(p-Bromophenyl)-3-(5'-hydroxymethyl-2'-furyl)indazole was obtained in a yield of 70%.

MS: m/z: 369 ($M^+$);

IR(KBr) $v_{max}$: 3500~3350 $cm^{-1}$ (—OH);

$^1$H-NMR(CDCl$_3$, 200 MHz) δ: 4.78 (2H, s, —CH$_2$C$_6$H$_5$), 6.51 (1H, d, J=3.3 Hz. C4'-H), 6.98 (1H, d, J=3.3 Hz, C3'-H), 7.27-7.73 (7H, m, Ar—H, C5, C6, C7), 8.16 (1H, d, J=8.1, C4-H);

Anal. Calc. for $C_{18}H_{13}BrN_2O_2$: C, (58.56); H, (3.55); N, (7.59).

Found: C, (58.52); H, (3.58); N, (7.64).

(b) Succinic acid mono-[5-(1-(4-bromo-phenyl)-1H-indazol-3-yl)-furan-2-ylmethyl]ester (Compound 12)

1-(p-Bromophenyl)-3-(5'-hydroxymethyl-2'-furyl)indazole was reacted with succinic anhydride according the procedure described in Example 1 (d) to afford Compound 12 in a yield of 76%.

m.p.: 111.0-112.7° C.;

MS(%): m/z: 469 ($M^+$);

IR(KBr) $v_{max}$: 3300~2500 $cm^{-1}$ (COOH); 1741 $cm^{-1}$ (C=O);

$^1$H-NMR(CDCl$_3$, 200 MHz) δ: 2.69 (4H, s, —COCH$_2$—), 5.24 (2H, s, —OCH$_2$—), 6.59 (1H, d, J=3.6 Hz, C4'-H), 6.97 (1H, d, J=3.4 Hz, C3'-H), 7.26-7.71 (7H, m, Ar, C5, C6, C7-H), 8.14 (1H, d, J=8.0 Hz, C4-H);

Anal. Calc. for $C_{22}H_{17}BrN_2O_5$: C, (56.31); H, (3.65); N, (5.97);

Found: C, (56.26); H, (3.62); N, (5.88).

EXAMPLE 13

Synthesis of {2-[5-(1-benzyl-1H-indazol-3yl)-furan-2-ylmethoxy]-ethyl}-dimethylamine (Compound 13)

NaH (80%, 1.5 g, 0.05 mole) was suspended in 10 ml THF. The suspension was stirred at 10±2° C., and a solution of 1-benzyl-3-(5'-hydroxymethyl-2'-furyl)indazole 0.01 mole) in 10 ml THF was added dropwise over 30 min. The reaction mixture was stirred at 25±2° C. and O-dimethylaminoethylchloride (5.38 g, 0.05 mole) was added. After the reaction mixture was refluxed for 10 min, the solvent was removed by evaporation. The residue was purified by column chromatography (SiO$_2$/toluene) to yield Compound 13 (25 mg, yield 75%) as a liquid.

MS: m/z: 375 ($M^+$), $^1$H-NMR (CDCl$_3$, 200 MHz) δ: 2.28 (6H, s, CH3*2), 2.55 (2H, t, J=5.6 Hz, —CH$_2$—CH$_2$—N), 3.63 (2H, t, J=5.6 Hz, —OCH$_2$CH$_2$—), 4.61 (2H, s, —CH2—O—), 5.54 (2H, s, N—CH2-C$_6$H$_5$), 6.01 (2H, s, —O—CH2-O—), 6.51 (1H, d, J=3.7 Hz, C4-H), 6.62 (1H, s, C7-H), 6.79 (1H, d, J=3.7 Hz, C3'-H), 7.15-7.37 (5H, m, Ar—H), 7.39 (1H, s, C4-H);

Anal. Calc. for $C_{23}H_{25}N_3O_2$: C, (73.57); H, (6.71); N, (11.20);

Found: C, (73.50); H, (6.70); N, (11.21).

EXAMPLE 14

Synthesis of [5-(1-benzyl-1H-indazol-3-yl)-furan-2-ylmethoxy]acetic acid (Compound 14)

(a) Synthesis of ethyl [5-(1-benzyl-1H-indazol-3-yl)-furan-2-ylmethoxy]acetate

1-Benzyl-3-(5'-hydroxymethyl-2'-furyl)indazole (600 mg, 2 mmole) was dissolved in dry THF (12 ml), and NaH (60% in oil, 110 mg, 2.8 mmole) was added portionwise with stirring at 40° C. Ethyl chloroacetate (500 mg, 4.08 mmole) was then added. After being stirred for 2 hrs at 60±2° C., the reaction mixture was poured into ice water, extracted with CHCl$_3$, and evaporated. The residue was purified by a silica gel column with CHCl$_3$ as eluent to afford ethyl [5-(1-benzyl-1H-indazol-3-yl)-furan-2-ylmethoxy]-acetate in a yield of 60%.

MS: m/z: 390($M^+$);

IR(KBr) $v_{max}$: 1720 $cm^{-1}$ (C=O);

$^1$H-NMR(CDCl$_3$, 200 MHz) δ: 1.25(3H, t, J=7.1 Hz, —CH$_3$), 4.16~4.27(4H, m, —OCH$_2$—, —OCH$_2$CO—), 4.74(2H, s, furanyl-CH$_2$O—), 5.64(2H, s, phenyl-CH$_2$—), 6.53(1H, d, J=3.3 Hz, C4'-H), 6.87(1H, d, J=3.3 Hz, C3'-H), 7.17~7.34(8H, m, C5, C6, C7, Ar—H), 8.08(1H, d, J=7.9 Hz, C4-H);

Anal. Calc. for C$_{23}$H$_{22}$N$_2$O$_4$: C, (70.75); H, (5.68); N, (7.17);

Found: C, (70.77); H, (5.67); N, (7.12).

(b) Synthesis of 2-{[5-(1-benzyl-1H-indazol-3-yl)-2-furyl]methoxy}-2-acetic acid (Compound 14)

Ethyl[5-(1-benzyl-1H-indazol-3-yl)-furan-2-ylmethoxy]acetate was suspended in 10% NaOH aqueous solution (1.1 mmole). The reaction mixture was refluxed for 2 hrs and then cooled to 30±2° C. Aqueous HCl (10%) was added until the pH value was 1-2. The resulting precipitate was collected by filtration and recrystallized from EtOH to give Compound 14 as a pale yellow needle.

m.p.: 86.0~86.9° C.;
MS: m/z: 362 (M$^+$);
IR(KBr) $v_{max}$: 3500~2700 cm$^{-1}$ (—COOH);
$^1$H-NMR(CDCl$_3$, 200 MHz) δ: 3.95(2H, s, —CH$_2$CO$_2$H); 4.50(2H, s, —CH$_2$O—5.53(2H, s, —CH$_2$C$_6$H$_5$); 6.12(1H, br, —OH); 6.29(1H, d, J=2.96 Hz, C4'-H); 6.65(1H, d, J=3.0 Hz, C3'-H); 7.03-7.26(8H, m, C5, C6, C7, Ar—H); 7.86(1H, d, J=8.0 Hz, C4-H);

Anal. Calc. For C$_{21}$H$_{18}$N$_2$O$_4$: C, (69.60); H, (5.01); N, (7.73);

Found: C, (69.65); H, (4.99); N, (7.70).

EXAMPLE 15

Synthesis of 5-[1-benzyl-(5-methylfuro[3,2-C]pyrazol-3-yl)furan-2-ylmethoxy]acetic acid (Compound 15)

(a) Synthesis of methyl 5-[1-(benzyl-5-methylfuro[3,2,-c]pyrazol-3-yl)furan-2-ylmethoxy]acetate 1-Benzyl-3-(5'-hydroxymethyl-2'-furyl)-5-methylfuro[3,2-C]pyrazole was dissolved in dry THF (12 ml), and NaH (60% in oil, 110 mg, 2.8 mmole) was added portionwise with stirring at 40° C. Ethyl chloroacetate (500 mg, 4.08 mmole) was then added. After being stirred for 2 hrs at 60±2° C., the reaction mixture was poured into ice water, extracted with CHCl$_3$, and evaporated. The residue was purified by a silica gel column with CHCl$_3$ as eluent to give methyl 5-[1-(benzyl-5-methylfuro[3,2,-c]pyrazol-3-yl)furan-2-ylmethoxy]acetate in a yield of 72%.

MS: m/z: 394(M$^+$);
IR(KBr) $v_{max}$: 1715 cm$^{-1}$ (C=O);
$^1$H-NMR(CDCl$_3$, 200 MHz) δ: 1.28(3H, t, J=7.1 Hz,), 2.34(3H, s, —CH$_3$), 4.17(2H, s, —OCH$_2$-furanyl), 4.22(2H, q, J=7.1 Hz, —OCH$_2$CH$_3$), 4.70 (2H, s, —OCH$_2$CO—), 5.35(2H, s, —CH$_2$C$_6$H$_5$), 5.58(1H, s, C7-H), 6.50(1H, d, J=3.3 Hz, C4'-H), 6.71(1H, d, J=3.3 Hz, C3'-H), 7.27-7.37 (5H, m, Ar—H);

Anal. Calc. for C$_{22}$H$_{22}$N$_2$O$_5$: C, (66.99); H, (5.62); N, (7.10);

Found: C, (66.85); H, (5.61); N, (7.12).

(b) Synthesis of 5-[1-benzyl-(5-methylfuro[3,2-C]pyrazol-3-yl)furan-2-yl-methoxy]acetic acid (Compound 15)

Compound 15 was obtained by hydrolysis of methyl 5-[1-(benzyl-5-methylfuro[3,2,-c]pyrazol-3-yl)furan-2-yl-methoxy]acetate according to the procedure described in Example 14(b) in a yield of 55%.

MS: m/z: 366(M$^+$);
IR(KBr) $v_{max}$: 3400-2550 cm$^{-1}$ (—COOH); 1730 cm$^{-1}$ (C=O);
$^1$H-NMR(CDCl$_3$, 200 MHz) δ: 2.34(3H, s, —CH$_3$), 4.06 (1H, s, —OH), 4.27(2H, s —OCH$_2$-furanyl), 4.70(2H, s, —OCH$_2$COOH), 5.42(2H, s, —CH$_2$C$_6$H$_5$), 5.57(1H, s, C7-H), 6.50(1H, d, J=3.3 Hz, C4'-H), 6.72(1H, d, J=3.3 Hz, C3'-H), 7.26-7.37(5H, m, Ar—H);

Anal. Calc. for C$_{20}$H$_{18}$N$_2$O$_5$: C, (65.57); H, (4.95); N, (21.84);

Found: C, (65.55); H, (4.98); N, (21.80).

EXAMPLE 16

Synthesis of 3-[5'-(β-dimethylaminoethoxy)methyl-2'-furyl]-5,6-methylenedioxy-1-benzylindazole (Compound 16)

(a) Synthesis of 3-(5'-hydroxymethyl-2'-furyl)-5,6-methylenedioxy-1-benzylindazole Reactions were carried out according to the same procedures described in Example 1 (b) and (c), except that methoxycarbonyl-2'-furyl-3,4-methylenedioxybenzoyl ketone was used instead of 5-methoxycarbonyl-2-furyl phenyl ketone. 3-(5'-Hydroxymethyl-2'-furyl)-5,6-methylene-dioxy-1-benzylindazole was obtained.

m.p.: 85-87° C.;
MS: m/z: 348(M$^+$);
$^1$H-NMR(CDCl$_3$, 200 MHz) δ: 4.71(2H, s, —CH$_2$OH), 5.53(2H, d, J=3.6 Hz, C3'-H), 6.00(2H, s, —OCH$_2$—O—), 6.44(1H, d, J=3.6 Hz, C4'-H), 6.61(1H, s, C7-H), 6.76(1H, d, J=3.6 Hz, C3'-H), 7.20-7.31(6H, m, C4-H, Ar—H);

Anal. Calc. for C$_{20}$H$_{16}$N$_2$O$_4$: C, (68.96); H, (4.63); N, (8.04);

Found: C, (68.84); H, (4.65); N, (8.08).

(b) Synthesis of 3-[5'-(D-dimethylaminoethoxy)methyl-2'-furyl]-5,6-methylene-dioxy-1-benzylindazole (Compound 16)

3-(5'-Hydroxymethyl-2'-furyl)-5,6-methylenedioxy-1-benzylindazole was reacted with β-dimethylaminoethylchloride according to the method described in Example 15(b) to afford Compound 16 as a pale oil in a yield of 76.1%.

MS: m/z: 419(M$^+$);
$^1$H-NMR(CDCl$_3$, 200 MHz) δ: 2.28(6H, s, —CH$_3$), 2.55 (2H, t, J=5.6 Hz, —OCH$_2$CH$_2$N—), 3.63(2H, t, J=5.6 Hz, —OCH$_2$CH$_2$N), 4.61(2H, s, —CH$_2$O—), 5.54(2H, s, —CH$_2$—N), 6.01(2H, s, —OCH$_2$O—), 6.51(1H, d, J=3.7 Hz, C4'-H), 6.62(1H, s, C7-H), 6.79(1H, d, J=3.7 Hz, C3'-H), 7.15-7.37(5H, m, Ar—H), 7.39(1H, s, C4-H);

Anal. Calc. for C$_{24}$H$_{25}$N$_3$O$_4$: C, (68.72); H, (6.01); N, (10.02);

Found: C, (68.80); H, (5.98); N, (10.05).

EXAMPLE 17

Synthesis of succinic acid mono-[5-(1-benzyl-1H-indazol-3-yl)-furan-2-ylmethyl]ester, ammonium salt (Compound 17)

Compound 1 (170 mg, 0.4 mmle) in 10 mL THF was treated with NH$_3$ at 25° C. After 30 mins, the precipitate formed in the reaction was filtered out to give Compound 17 in a yield of 90%.

MS: m/z: 421(M+);

IR(KBr) $\nu_{max}$: 3500~2500 cm$^{-1}$ (—COOH); 1740 cm$^{-1}$ (—C=O);

$^1$H-NMR(CDCl$_3$, 200 MHz) δ: 2.67 (4H, s, —COCH$_2$—), 5.22 (2H, s, —OCH$_2$—), 5.65 (2H, s, —CH$_2$C$_6$H$_5$), 6.56 (1H, d, J=3.3 Hz, C4'-H), 6.87 (1H, d, J=3.3 Hz, C3'-H), 7.19-7.36 (7H, m, Ar, C5, C6, C7-H), 8.04 (1H, d, J=7.9 Hz, C4-H).

EXAMPLE 18

Inhibition of Cancer Cell Growth by Compound 1

Human lung cancer cells, NCI-H226, were placed in 96-well microtiter plates (5,000 cells/100 μl/well). The plates were incubated at 37° C. under 5% CO$_2$ and 95% air and 100% relative humidity for 24 hr. Cells in one plate were fixed in situ with trichloroacetic acid (TCA) to measure the cell population.

Compound 1 was dissolved in dimethylsulfoxide (DMSO) to give a solution at 400-fold the desired final maximum test concentration and stored frozen. An aliquot of the frozen DMSO solution was thawed and diluted to twice the desired final maximum test concentration. Additional ½ log serial dilutions were made to provide a total of eight concentrations. 100 μl aliquots of these different dilutions were added to the microtiter wells, resulting in the required final drug concentrations. After Compound 1 was added, the plates were incubated at 37° C. under 5% CO$_2$ and 95% air and 100% relative humidity for an additional 48 hr. The cells were fixed in situ by slow addition of 50 μl of cold 50% (w/v) TCA and incubated at 4° C. for 60 minutes. The supernatant was removed, and the plates were gently washed twice with water and air-dried. The cells in each well were dyed with a 1% acetic acid solution of sulforhodamine B (100 μl), an anionic protein stain, and incubated at room temperature for 10 minutes. The unbound stain was removed by gently washing twice with 1% acetic acid and the plates were air-dried. The bound stain was subsequently solubilized with 10 mM trizma base, and absorbance was measured by an automated plate reader at the wavelength of 515 nm. The results show that Compound 1 effectively inhibited growth of NCI—H226.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A compound of the following formula:

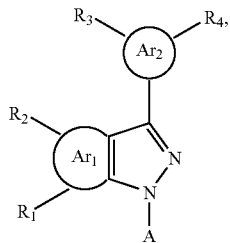

wherein
A is

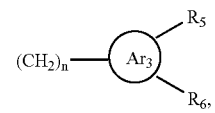

in which n is 0, 1, 2, or 3;
Ar$_1$ is benzene, thiophene, or furan;
Ar$_2$ is furyl;
Ar$_3$ is phenyl;
R$_1$ and R$_2$ are independently hydrogen, halogen, or —(CH$_2$)$_m$OR$^e$;
R$_3$ is H or alkyl;
R$_4$ is (CR$^a$R$^b$)$_p$X(CR$^c$R$^d$)$_q$Y,
R$_5$ and R$_6$ are independently hydrogen, halogen, or alkyl, or R$_5$ and R$_6$ together form O(CH$_2$)$_m$O—;
X is —O—, —S—, —NR$^{a_1}$—, —O—C(O)—, or —C(O)—O—;
Y is —C(O)OR$^{c_1}$, —NR$^{c_1}$R$^{d_1}$, —C(O)NR$^{c_1}$R$^{d_1}$, —SO$_3$R$^{c_1}$, —SO$_2$NR$^{c_1}$R$^{d_1}$, —SONR$^{c_1}$R$^{d_1}$, or —P(O)(OR$^{c_1}$)(OR$^{d_1}$);
R$^a$, R$^b$, R$^c$, and R$^d$ are independently H, halogen, nitro, cyano, alkyl, or aryl;
R$^e$ is H, alkyl, or halogen;
R$^{a_1}$, R$^{c_1}$, and R$^{d_1}$ are independently H, alkyl, or aryl;
m is 0, 1, 2, 3, 4, 5, or 6; and
p and q are independently 1, 2, 3, 4, 5, or 6; or a salt thereof.

2. The compound of claim 1, wherein R$_3$ is H and R$_4$ is (CR$^a$R$^b$)$_p$X(CR$^c$R$^d$)$_q$Y bonded to position 5 of furyl.

3. The compound of claim 1, wherein X is —O— or —O—C(O)—.

4. The compound of claim 3, wherein Y is —COOH or —NR$^{c_1}$R$^{d_1}$, in which each of R$^{c_1}$ and R$^{d_1}$, independently, is H or alkyl.

5. The compound of claim 1, wherein Ar$_1$ is phenyl.

6. The compound of claim 5, wherein A is CH$_2$Ph.

7. The compound of claim 6, wherein X is —O—, —S—, NR$^{a_1}$, —O—C(O)—, or —C(O)—O—.

8. The compound of claim 7, wherein X is —O— or —O—C(O)—.

9. The compound of claim 8, wherein Y is —COOH or —NR$^{c_1}$R$^{d_1}$, in which each of R$^{c_1}$ and R$^{d_1}$, independently, is H or alkyl.

10. The compound of claim 1, wherein the compound is
succinic acid mono-[5-(1-benzyl-1H-indazol-3-yl)-furan-2-ylmethyl]ester,
succinic acid mono-[5-(1-benzyl-1H-indazol-3-yl)-furan-2-ylmethyl]ester, sodium salt, succinic acid mono-[5-(1-benzyl-6-methoxy-1H-indazol-3-yl)-furan-2-ylmethyl]ester, succinic acid mono-[5-(1-benzyl-5-methoxy-1H-indazol-3-yl)-furan-2-ylmethyl]ester, succinic acid mono-[5-(1-benzyl-6-fluoro-1H-indazol-3-yl)-furan-2-ylmethy]ester, succinic acid mono-[5-(1-benzyl-6-methyl-1H-indazol-3-yl)-furan-2-ylmethyl]ester, succinic acid mono-[5-(1-benzyl-5-methyl-1H-furo[3,2-C]pyrazol-3-yl)-furan-2-ylmethyl]ester, succinic acid mono-[5-(1-benzyl-1H-thieno[3,2-C]pyrazol-3-yl)-furan-2-ylmethyl]ester succinic acid mono-[4-(1-benzyl-1H-indazol-3-yl)benzyl]ester, succinic acid mono-[5-(1-(4-chloro-benzyl)-1H-indazol-3-yl)-furan-2-ylmethy]ester, succinic acid mono-[5-(6-methoxy-1-phenyl-1H-indazol-3-yl)-furan-2-ylmethyl]ester, succinic acid mono-[5-(1-(4-bromo-phenyl)-1H-indazol-3-yl)-furan-2-ylmethyl]ester, {2-[5-(1-benzyl-1H-indazol-3yl)-furan-2-ylmethoxy]-ethyl}-dimethylamine, [5-(1-benzyl-1H-indazol-3-yl)-furan-2-ylmethoxy]acetic acid, 5-[1-benzyl-(5-methylfuro[3,2-C]pyrazol-3-yl)furan-2-ylmethoxy]acetic acid, 3-[5'-(β-dimethylaminoethoxy)methyl-2'-furyl]-5,6-methylenedioxy-1-benzylindazole, or succinic acid mono-[5-(1-benzyl-1H-indazol-3-yl)-furan-2-ylmethyl]ester, ammonium salt.

11. A pharmaceutical composition, comprising an effective amount of a compound of the following formula:

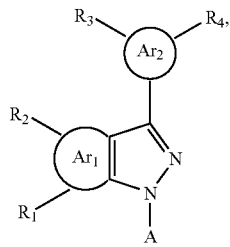

wherein

A is

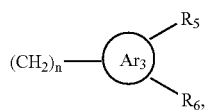

in which n is 0, 1, 2, or 3;

Ar$_1$ is benzene, thiophene, or furan;

Ar$_2$ is furyl;

Ar$_3$ is phenyl;

R$_1$ and R$_2$ are independently hydrogen, halogen, or —(CH$_2$)$_m$OR$^e$;

R$_3$ is H or alkyl;

R$_4$ is (CR$^a$R$^b$)$_p$X(CR$^c$R$^d$)$_q$Y;

R$_5$ and R$_6$ are independently hydrogen, halogen, or alkyl, or R$_5$ and R$_6$ together form O(CH$_2$)$_m$O—;

X is —O—, —S—, —NR$^{a1}$—, —O—C(O)—, or —C(O)—O—;

Y is —C(O)OR$^{c1}$, —NR$^a$R$^{d1}$, —C(O)NR$^a$R$^{d1}$, —SO$_3$R$^{c1}$, —SO$_2$NR$^a$R$^{d1}$, —SONR$^a$R$^{d1}$, or —P(O)(OR$^{c1}$)(OR$^{d1}$);

R$^a$, R$^b$, R$^c$, and R$^d$ are independently H, halogen, nitro, cyano, alkyl, or aryl;

R$^e$ is H, alkyl, or halogen;

R$^{a1}$, R$^{c1}$, and R$^{d1}$ are independently H, alkyl, or aryl;

m is 0, 1, 2, 3, 4, 5, or 6; and p and q are independently 1, 2, 3, 4, 5, or 6;

or a pharmaceutically acceptable salt thereof; and a pharmaceutically acceptable carrier.

12. The composition of claim 11, wherein R$_3$ is H and R$_4$ is (CR$^a$R$^b$)$_p$X(CR$^c$R$^d$)$_q$Y bonded to position 5 of furyl.

13. The composition of claim 11, wherein X is —O— or —O—C(O).

14. The composition of claim 13, wherein Y is —COOH or —NR$^{c1}$R$^{d1}$, in which each of R$^{c1}$ and R$^{d1}$, independently, is H or alkyl.

15. The composition of claim 11, wherein Ar$_1$ is phenyl.

16. The composition of claim 15, wherein A is CH$_2$Ph.

17. The composition of claim 16, wherein X is —O—, —S—, —NR$^{a1}$—, —O—C(O)—, or —C(O)—O—.

18. The composition of claim 17, wherein X is —O— or —O—C(O).

19. The composition of claim 18, wherein Y is —COOH or —NR$^{c1}$R$^{d1}$, in which each of R$^{c1}$ and R$^{d1}$, independently, is H or alkyl.

20. The composition of claim 11, wherein the compound is succinic acid mono-[5-(1-benzyl-1H-indazol-3-yl)-furan-2-ylmethyl]ester, succinic acid mono-[5-(1-benzyl-1H-indazol-3-yl)-furan-2-ylmethyl]ester, sodium salt, succinic acid mono-[5-(1-benzyl-6-methoxy-1H-indazol-3-yl)-furan-2-ylmethyl]ester, succinic acid mono-[5-(1-benzyl-5-methoxy-1H-indazol-3-yl)-furan-2-ylmethyl]ester, succinic acid mono-[5-(1-benzyl-6-fluoro-1H-indazol-3-yl)-furan-2-ylmethy]ester, succinic acid mono-[5-(1-benzyl-6-methyl-1H-indazol-3-yl)furan-2-ylmethyl]ester, succinic acid mono-[5-(1-benzyl-5-methyl-1H-furo[3,2-C]pyrazol-3-yl)-furan-2-ylmethyl]ester, succinic acid mono-[5-(1-benzyl-1H-thieno[3,2-C]pyrazol-3-yl)-furan-2-ylmethyl]ester succinic acid mono-[4-(1-benzyl-1H-indazol-3-yl)benzyl]ester, succinic acid mono-[5-(1-(4-chloro-benzyl)-1H-indazol-3-yl)-furan-2-ylmethy]ester, succinic acid mono-[5-(6-methoxy-1-phenyl-1H-indazol-3-yl)-furan-2-ylmethyl]ester, succinic acid mono-[5-(1-(4-bromo-phenyl)-1H-indazol-3-yl)-furan-2-ylmethyl]ester, {2-[5-(1-benzyl-1H-indazol-3yl)-furan-2-ylmethoxy]-ethyl}-dimethylamine,

[5-(1-benzyl-1H-indazol-3-yl)-furan-2-ylmethoxy]acetic acid,

5-[1-benzyl-(5-methylfuro[3,2-C]pyrazol-3-yl)furan-2-ylmethoxy]acetic acid,

3-[5'-(β-dimethylaminoethoxy)methyl-2'-furyl]-5,6-methylenedioxy-1-benzylindazole, or succinic acid mono-[5-(1-benzyl-1H-indazol-3-yl)-furan-2-ylmethyl]ester, ammonium salt.

21. The compound of claim 1, wherein Ar$_1$ is benzene or thiophene.

22. The compound of claim 10, wherein the compound is
succinic acid mono-[5-(1-benzyl-1H-indazol-3-yl)-furan-2-ylmethyl]ester,
succinic acid mono-[5-(1-benzyl-1H-indazol-3-yl)-furan-2-ylmethyl]ester, sodium salt, or
succinic acid mono-[5-(1-benzyl-1H-indazol-3-yl)-furan-2-ylmethyl]ester, ammonium salt.

23. The composition of claim 11, wherein $Ar_1$ is benzene or thiophene.

24. The composition of claim 20, wherein the compound is
succinic acid mono-[5-(1-benzyl-1H-indazol-3-yl)-furan-2-ylmethyl]ester,
succinic acid mono-[5-(1-benzyl-1H-indazol-3-yl)-furan-2-ylmethyl]ester, sodium salt, or
succinic acid mono-[5-(1-benzyl-1H-indazol-3-yl)-furan-2-ylmethyl]ester, ammonium salt.

* * * * *